United States Patent
Berguer et al.

(10) Patent No.: US 9,072,445 B2
(45) Date of Patent: Jul. 7, 2015

(54) COMMON BILE DUCT SURGICAL IMAGING SYSTEM

(75) Inventors: Ramon Berguer, Novato, CA (US); Michael Robert Gluszczak, San Jose, CA (US)

(73) Assignee: LIFEGUARD SURGICAL SYSTEMS INC., Novato, CA (US)

(*) Notice: Subject to any disclaimer, the term of this patent is extended or adjusted under 35 U.S.C. 154(b) by 1348 days.

(21) Appl. No.: 12/011,490

(22) Filed: Jan. 24, 2008

(65) Prior Publication Data
US 2009/0192349 A1    Jul. 30, 2009

(51) Int. Cl.
*A61B 1/06*    (2006.01)
*A61B 1/04*    (2006.01)
*A61B 1/313*   (2006.01)
*A61B 5/00*    (2006.01)
*A61B 19/00*   (2006.01)

(52) U.S. Cl.
CPC .............. *A61B 1/043* (2013.01); *A61B 1/3132* (2013.01); *A61B 5/0071* (2013.01); *A61B 5/0086* (2013.01); *A61B 19/5225* (2013.01); *A61B 2019/5289* (2013.01); *A61B 2019/5291* (2013.01)

(58) Field of Classification Search
CPC ........... A61B 1/00121; A61B 1/00124; A61B 1/00126; A61B 1/00128; A61B 1/04; A61B 1/042; A61B 1/043; A61B 1/045; A61B 1/313
USPC ......... 600/109, 111, 113, 160, 166, 168, 170, 600/171, 178, 181, 476, 478, 131, 132, 136, 600/172, 174
See application file for complete search history.

(56) References Cited

U.S. PATENT DOCUMENTS

| 5,224,931 A | 7/1993 | Kumar |
| 5,507,287 A | 4/1996 | Palcic et al. |

(Continued)

FOREIGN PATENT DOCUMENTS

| WO | WO 99/01749 A | 1/1999 |
| WO | WO 2005/034747 A | 4/2005 |

OTHER PUBLICATIONS

Patent Cooperation Treaty, Application No. PCT/US2009/031712, International Search Report and Written Opinion, dated Apr. 22, 2009.

(Continued)

*Primary Examiner* — Anhtuan T Nguyen
*Assistant Examiner* — William Chou
(74) *Attorney, Agent, or Firm* — Wilson Sonsini Goodrich & Rosati

(57) ABSTRACT

A method and apparatus for imaging features of a CBD in a patient introduces a fluorescent contrast agent into the CBD. A light source transmits both a visible light and a fluorescent light into a patient's abdominal cavity via the laparoscope. Cameras attached to or integrated into the laparoscope detect visible light images and fluorescent emission light images. The visible light image and fluorescent image signals are processed to combine the fluorescent emission light image signals and visible image signals into a single display signal. The system adjusts the display characteristics, such as color, of the fluorescent emission light image so it contrasts well with the visual light image so the surgeon can easily distinguish between the two images. The display signal is sent to a video monitor where the surgeon views the visible light image and the fluorescent image as a single overlaid image.

9 Claims, 10 Drawing Sheets

(56) References Cited

U.S. PATENT DOCUMENTS

| | | | |
|---|---|---|---|
| 5,590,660 A | 1/1997 | MacAulay et al. | |
| 5,647,368 A | 7/1997 | Zeng et al. | |
| 5,769,792 A | 6/1998 | Palcic et al. | |
| 5,827,190 A | 10/1998 | Palcic et al. | |
| 5,833,596 A | 11/1998 | Bonnell et al. | |
| 5,879,306 A | 3/1999 | Fontenot et al. | |
| 5,910,816 A | 6/1999 | Fontenot et al. | |
| 5,944,653 A | 8/1999 | Bonnell et al. | |
| 6,192,267 B1 | 2/2001 | Scherninski et al. | |
| 6,293,911 B1 * | 9/2001 | Imaizumi et al. | 600/160 |
| 6,636,755 B2 | 10/2003 | Toida | |
| 6,804,549 B2 | 10/2004 | Hayashi | |
| 6,899,675 B2 | 5/2005 | Cline et al. | |
| 6,915,154 B1 | 7/2005 | Docherty et al. | |
| 6,960,165 B2 | 11/2005 | Ueno et al. | |
| 7,016,717 B2 | 3/2006 | Demos et al. | |
| 7,149,567 B2 | 12/2006 | Demos et al. | |
| 7,179,222 B2 | 2/2007 | Imaizumi et al. | |
| 7,221,388 B2 | 5/2007 | Sudo et al. | |
| 7,257,437 B2 | 8/2007 | Demos et al. | |
| 8,599,250 B2 * | 12/2013 | Amling et al. | 348/65 |
| 2002/0093563 A1 * | 7/2002 | Cline et al. | 348/65 |
| 2002/0161282 A1 * | 10/2002 | Fulghum | 600/160 |
| 2003/0078477 A1 * | 4/2003 | Kang et al. | 600/178 |
| 2003/0153825 A1 * | 8/2003 | Mooradian et al. | 600/407 |
| 2004/0006276 A1 | 1/2004 | Demos et al. | |
| 2004/0186351 A1 * | 9/2004 | Imaizumi et al. | 600/160 |
| 2005/0059894 A1 * | 3/2005 | Zeng et al. | 600/476 |
| 2005/0182321 A1 * | 8/2005 | Frangioni | 600/431 |
| 2006/0239921 A1 | 10/2006 | Mangat et al. | |
| 2006/0247537 A1 * | 11/2006 | Matsumoto | 600/478 |
| 2007/0073104 A1 * | 3/2007 | Iketani et al. | 600/109 |
| 2007/0135805 A1 | 6/2007 | Peyman | |
| 2008/0139881 A1 | 6/2008 | Cover et al. | |
| 2008/0154102 A1 | 6/2008 | Frangioni et al. | |
| 2008/0249400 A1 * | 10/2008 | Golijanin et al. | 600/431 |
| 2008/0255460 A1 * | 10/2008 | Voegele et al. | 600/476 |
| 2009/0118578 A1 * | 5/2009 | Takasugi et al. | 600/109 |
| 2009/0192390 A1 | 7/2009 | Berguer et al. | |
| 2009/0234234 A1 * | 9/2009 | Machida | 600/476 |

OTHER PUBLICATIONS

Patent Cooperation Treaty, Application No. PCT/US2009/031712, Current Claims as of Apr. 22, 2009.

* cited by examiner

COMMON BILE DUCT SURGICAL IMAGING SYSTEM

FIELD OF THE INVENTION

The present invention relates to surgical imaging systems. In particular, gall bladder surgical imaging systems.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Gallbladder surgery is currently performed using a laparoscopic technique. The surgeon inserts several tubes, called trocars or ports, into the abdominal cavity during this type of surgery. A 10 mm diameter optical scope, a laparoscope, is inserted into one of the ports. The laparoscope is attached to a video camera that allows the surgeon and the surgical team to view the inside of the abdominal cavity on a video screen. Long, slender instruments are passed through the other ports to grasp, dissect, and cut the tissue.

Laparoscopic surgery requires extra training in order to work with the new instruments and maneuver using a 2-D view of the surgical field. As a result of the limitations of this technique, inadvertent injuries to vital structures occur at a higher rate than in open surgery, even among experienced surgeons. The most serious complication of gallbladder surgery occurs when the surgeon inadvertently injures or cuts the common bile duct (CBD). This complication occurs in 1/200 (0.5%) operations in the U.S. Thus, of the approximately 800,000 laparoscopic gallbladder operations performed each year in the U.S., about 4000 patients will suffer a CBD injury.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1:
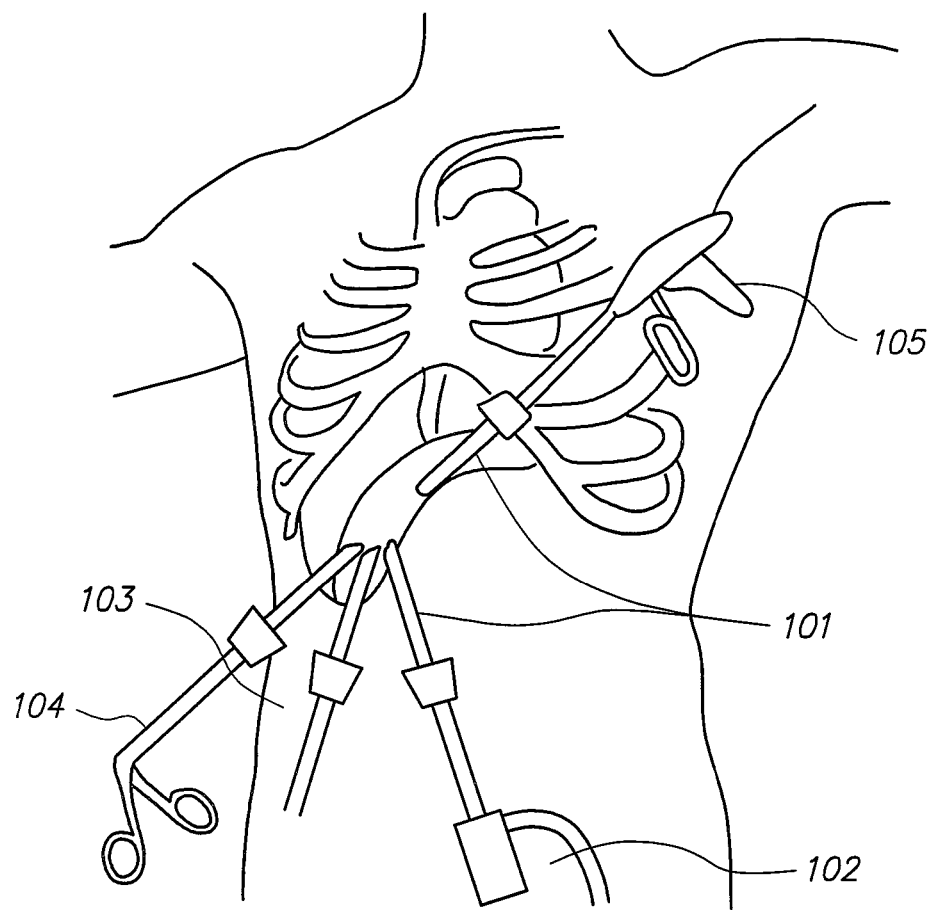
FIG. 1 is a diagram illustrating a surgical instrument used during laparoscopic surgery according to an embodiment of the invention.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

In the following discussion, in references to the drawings like numerals refer to like parts throughout the several views.

Embodiments are described herein according to the following outline:
- 1.0 General Overview
- 2.0 System Structural Overview
- 3.0 Example Techniques and Processes
  - 3.1 Common Bile Duct Imaging System
  - 3.2 Imaging System Optical Layout
- 4.0 Common Bile Duct Fluorescence and Display
- 5.0 Implementation Mechanisms—Hardware Overview

1.0 General Overview

Embodiments of the invention summarized above are described below in greater detail, along with some alternative embodiments of the invention. Although embodiments of the invention described below are described in the context of laparoscopic surgery of the common bile duct (CBD), in alternative embodiments of the invention, applications other than laparoscopic surgery may be substituted for, and may perform similar operations to those that are performed in laparoscopic surgery of the common bile duct.

An embodiment introduces a fluorescent contrast agent into the CBD via direct injection into the gallbladder, the cystic duct, the CBD, or via intravenous injection and excretion of the contrast agent by the liver into the bile. A light source illuminates a light path in a laparoscope. The light source transmits both a visible light and an infrared (IR) light (otherwise known as a fluorescent excitation light) into a patient's abdominal cavity via the laparoscope. The fluorescent contrast agent is excited by the narrow band light energy and produces light emission in a certain wavelength band. A camera assembly on the laparoscope can be communicatively connected to camera controller via an electronic cable, or wirelessly via Bluetooth (or any wireless technology) or a wireless local area network. The camera assembly contains both a visible light detection camera and an IR light detection camera. The cameras attached to the laparoscope detect visible light images and fluorescent emission light images.

The visible light image and fluorescent image signals from the camera assembly are processed to combine the fluorescent emission light image signals and visible image signals into a single display signal in order to overlay (or combine) the two images in their proper alignment. The system adjusts the display characteristics, such as color, of the fluorescent emission light image so it contrasts well with the visual light image so the surgeon can easily distinguish between the two images.

The display signal is sent to a video monitor where the surgeon views the visible light image and the fluorescent image as a single overlaid (or combined) image. The surgeon can instruct the system to display the fluorescent image in a desired color so the fluorescent image is properly contrasted to the visible image.

The overlay image can be turned on or off by the user via a switch or software control. The system can handle multiple displays with different combinations of images. A sensor may be included in the camera housing which allows the user to know which direction the ground or sky is. This allows the surgeon to select and display the orientation of the camera as referenced to the sky or the ground. This could be very helpful in NOTES type of operations as well (discussed below).

The system can record the combined visual and fluorescent images on an external or internal digital recording device such as CD, DVD, optical disk, hard disk, or flash memory. The system has an Ethernet connection to allow Internet or intranet connectivity so that recordings may be made to a server or transmitted over the Internet or intranet.

2.0 System Structural Overview

Referring to FIG. 1, as mentioned above, during gallbladder surgery, the surgeon inserts several tubes 101, called trocars or ports, into the abdominal cavity. A 10 mm diameter optical scope, a laparoscope 102, is inserted into one of the ports. The laparoscope is attached to a video camera that allows the surgeon and the surgical team to view the inside of the abdominal cavity on a video screen. Long, slender instruments 103, 104, 105, are passed through the other ports to grasp, dissect, and cut the tissue.

Figure 2:
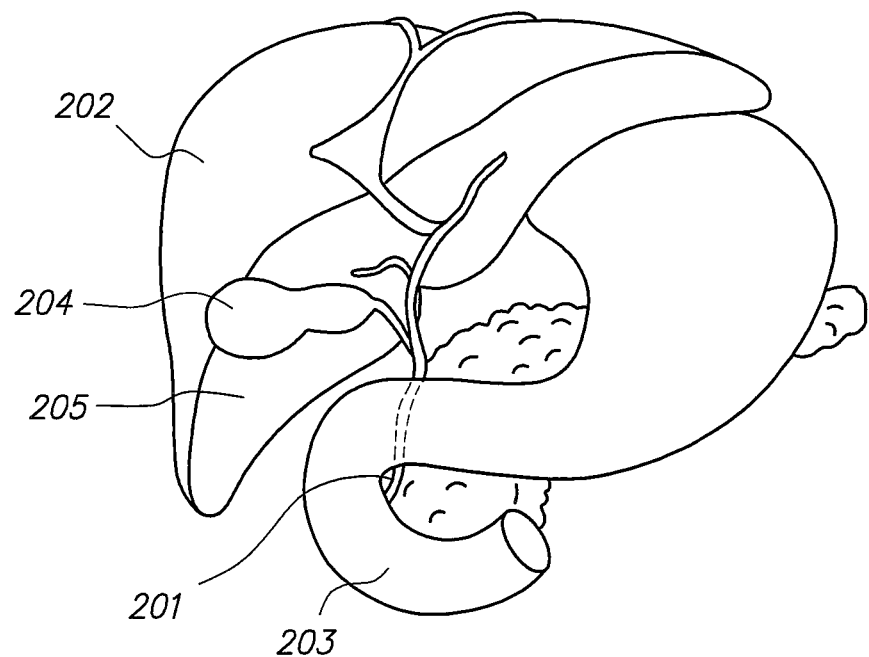
FIG. 2 is a diagram illustrating the bile duct anatomy.

FIG. 2 illustrates the bile duct anatomy. The common bile duct (CBD) 201 carries the bile from the liver 202 to the intestine 203 for digestion. The gallbladder 204 is a side pouch that stores bile, and squeezes into the CBD 201 during meals. The gallbladder 204 is attached to the CBD 201 by the cystic duct 205. The cystic duct 205 must be clearly identified by the surgeon, clipped or ligated, and then cut with scissors. If the surgeon mistakes the CBD 201 for the cystic duct 205, a CBD injury will occur. If the surgeon uses electrocautery energy to coagulate bleeding near the CBD 201 he may injure the CBD 201.

Figure 3:
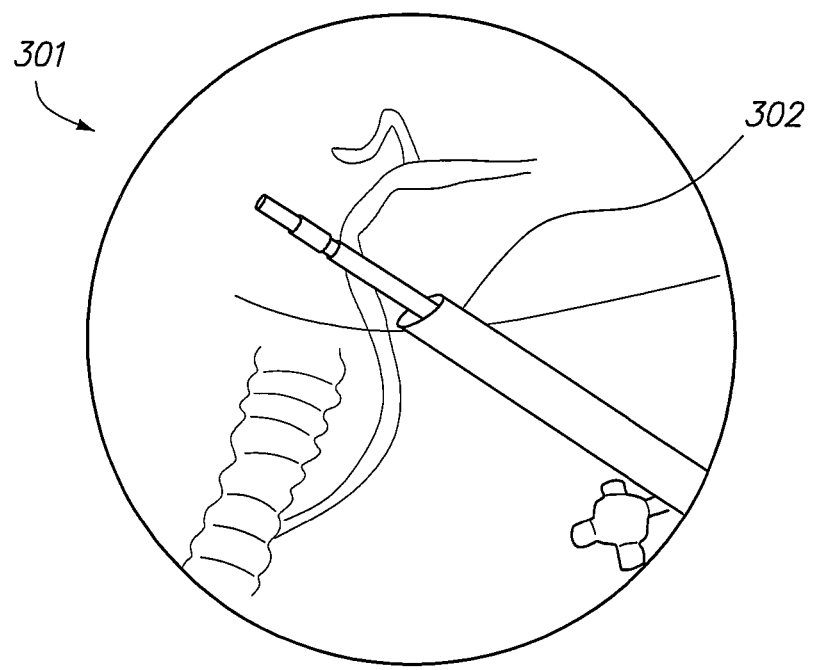
FIG. 3 is a diagram illustrating an intraoperative cholangiogram (IOC)

The only way to see the CBD at present is to do an intraoperative cholangiogram (IOC). This involves placing a catheter into the cystic duct 205 during surgery, injecting x-ray contrast liquid, and using an overhead or portable fluoroscopy device to see the x-ray outline made by the dye. This gives an indication of the shape and course of the CBD 201 and the biliary tree. As shown in FIG. 3, the IOC picture 301 is displayed on a black and white screen and can be printed or saved. Performing an IOC is not considered standard of care and is not done in all operations due to the cost, time, and trouble of performing it. In addition, x-ray exposure to the patient and surgical staff is a concern. The patient is exposed to x-ray radiation for that particular surgical procedure. However, the operating room staff is exposed each time this type of procedure is performed. Nevertheless, studies have shown that when surgeons perform an IOC, their patients sustain half the CBD injuries compared to those patients who did not have an IOC performed.

It is clear that performing gallbladder surgery safely requires the surgeon to view the CBD. However, it is not directly viewable as it lies beneath 1-3 mm of overlying fatty tissue and peritoneum. The safest and most useful way to view the CBD is to provide the surgeon with a "live", real-time (or near real-time), image of the location and course of the CBD during the operation—in essence a real-time IOC. This allows the surgeon to be aware of the position of the CBD at all times enabling him to avoid accidental or unintentional injury to the CBD. This has not previously been done because there had been no reliable and simple method to visualize the CBD which lies deep from the visible surface during laparoscopic surgery. An embodiment images the bile duct during gallbladder surgery and presents the CBD image as a real-time display for the surgeon. This device can reduce the CBD injury rate by at least 50% or perhaps more, thereby saving approximately 2000 patients per year (in the U.S.) from the pain and suffering resulting from a CBD injury and speed up all procedures since the CBD can be quickly identified and avoided.

3.0 Example Techniques and Processes 3.1 Common Bile Duct Imaging System

Embodiments can be built as either an add-on to current laparoscopic systems or as an integrated standalone system. The embodiments allow the surgeon to see the CBD in its proper position during gallbladder surgery.

Figure 4:
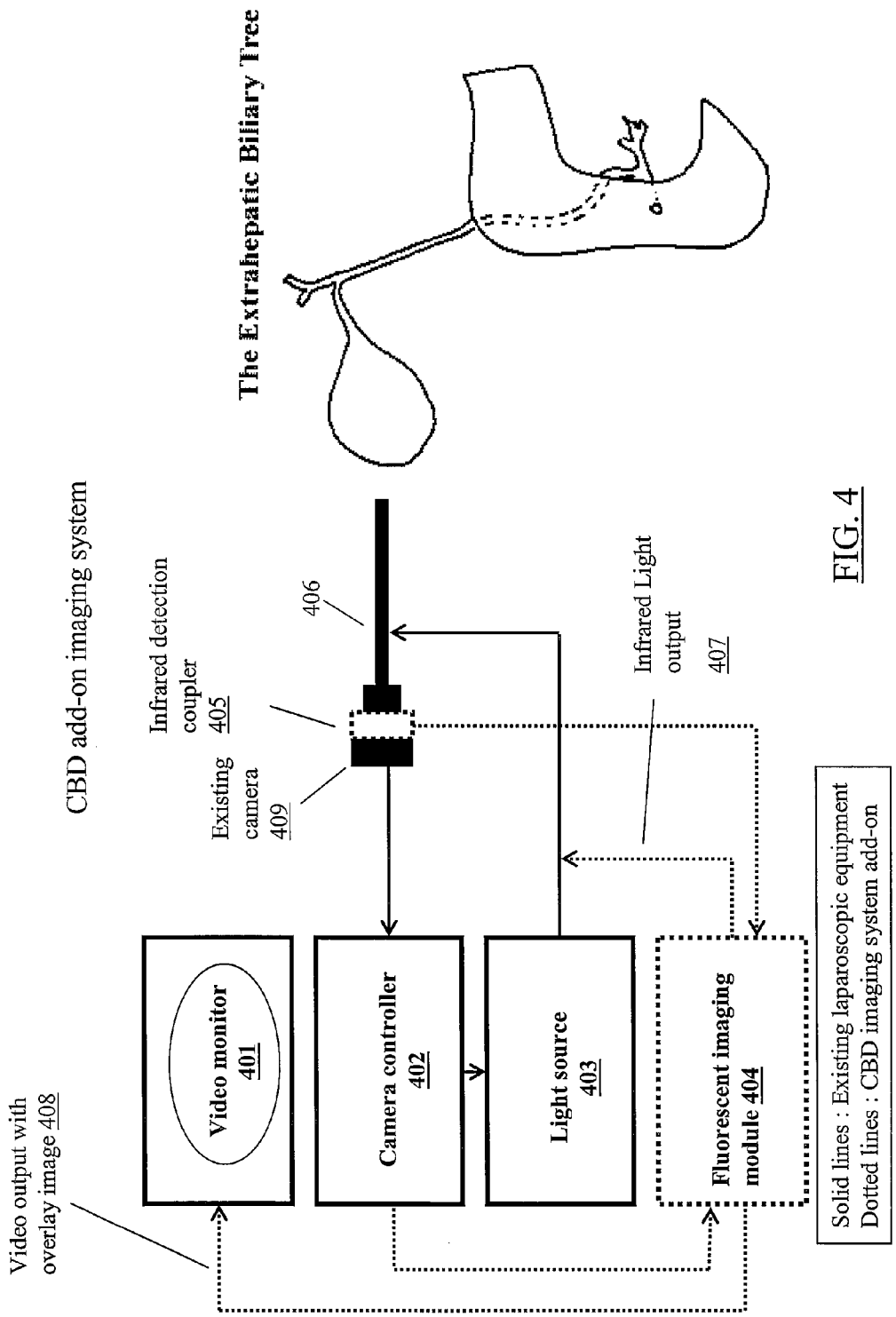
FIG. 4 is a block diagram illustrating an add-on configuration of a common bile duct imaging system according to an embodiment of the invention.

FIG. 4 shows an embodiment of an add-on configuration that integrates with current laparoscopic light sources and video systems. A fluorescent imaging module 404 introduces IR light 407 into the existing fiberoptic lighting system 403 and through the light channel of the laparoscope 406. An infrared detection coupler 405 is added to the laparoscope 406 between the laparoscope and visible light camera 409. The infrared detection coupler 405 contains a camera that is capable of detecting an IR signal from a fluorescent marker or tissue auto-fluorescence. The infrared detection coupler 405 is communicatively connected to the fluorescent imaging module 404. The connectors may be electronic cables, fiberoptic cables, a wireless transmission system, or any combination and/or quantity thereof. The connection cables may be disposable or reusable and may need to be sterilized if they contact the sterile surgical field. Alternatively, the IR image may be transmitted via an optical path to a remote IR camera (that may be located near the fluorescent imaging module 404). This may be necessary in case the size of an IR camera is not compatible with the coupler 405 size specifications.

During operation, the light source 403 transmits visible light through the fiberoptics in the laparoscope 406. The fluorescent imaging module 404 transmits IR light (fluorescent excitation light) through the fiberoptics in the laparoscope 406 at the same time. The camera controller 402 receives visible light image signals (the actual view of the surgical field using visible light) from the existing camera 409 mounted to the laparoscope 406. The camera controller 402 processes the visible light image signals into visible image display signals and sends the visible image display signals to the fluorescent imaging module 404.

The fluorescent imaging module 404 receives IR (fluorescent) light image signals from the infrared detection coupler 405. It processes the fluorescent emission light image signals along with the visible image display signals received from the camera controller 402 to create a video output signal 408 that contains a real-time overlay (or combination) of the fluorescent emission light image signals and visible image display signals. The fluorescent imaging module 404 digitally processes the fluorescent emission light image signals using a computer system or dedicated microprocessor to create a pleasing and natural graphics display of the CBD. The fluorescent imaging module 404 can use any known technique to combine the fluorescent emission light image signals and visible image display signals into a single display signal in order to overlay the two images in their proper alignment. This can include a simple reliance on a common focus point where the two cameras are aligned before surgery and the two image signals are combined in a straightforward manner, or using software to automatically detect common reference points within the two image signals in order to properly align the two images.

The video output signal 408 is sent to a video monitor 401 where the surgeon views the visible light image and the fluorescent image as a single overlaid image. The surgeon can instruct the fluorescent imaging module 404 to display the fluorescent image in a desired color, shape, or texture so the fluorescent image is properly contrasted to the visible image.

Alternatively, the add-on system may need to replace one of the components of current laparoscopic systems, either the camera head 409, the camera controller 402, or the light source 403. In that case, the system interfaces with the remaining components either at the input or output of those devices.

Figure 5:
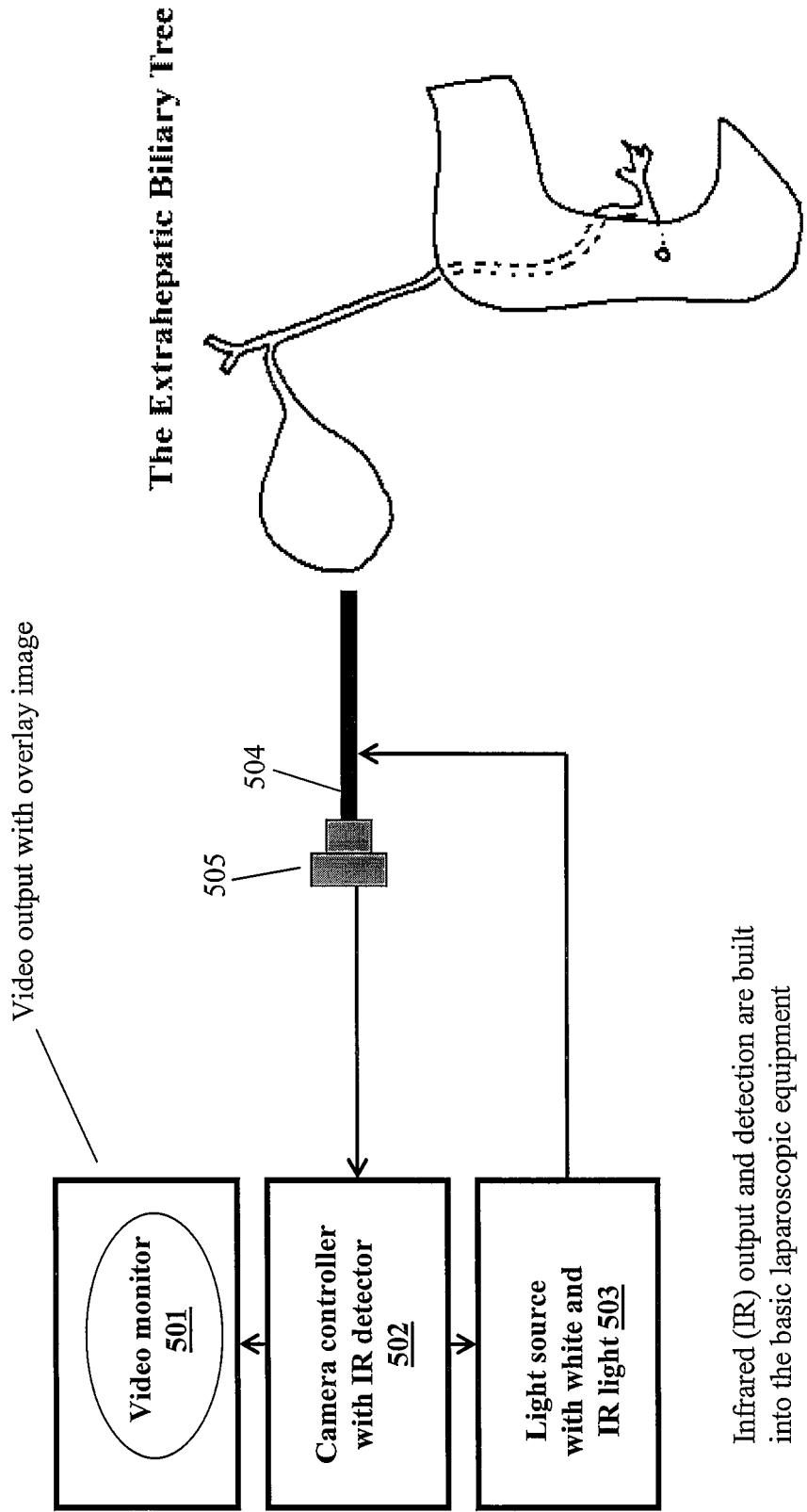
FIG. 5 is a block diagram illustrating a standalone configuration of a common bile duct imaging system according to an embodiment of the invention.

FIG. 5 illustrates an embodiment that is a standalone CBD imaging system that integrates the IR light source, IR detection system, visible light source, and visible image detection system into a complete and standalone laparoscopic imaging system with enhanced optical capabilities. The embodiment incorporates both a visible light camera and an IR light camera into a single camera enclosure 505 that attaches to the laparoscope 504 or is integrated into the laparoscope 504. The light source 503 transmits both visible light and IR light to fiberoptics in the laparoscope 504. Alternatively, the visible and IR light sources can be integrated into the laparoscope 504 itself or into a trocar to eliminate the need for fiberoptic cables to be connected from the camera controller 502 to the laparoscope 504, thus, making the laparoscope assembly lighter and easier to maneuver.

During normal operations, the light source 503 is instructed by the camera controller 502 to illuminate the light path in the laparoscope 504. The light source 503 transmits both (depending on the request) a visible light and an IR light to the laparoscope 504. The camera controller 504 receives signals from cameras in the laparoscope 504. The camera assembly 505 can be communicatively connected to camera controller 504 via an electronic cable, fiberoptic cable, wirelessly via Bluetooth (or any wireless technology) or a wireless local area network, or any combination and/or quantity thereof. The camera assembly 505 contains both a visible light detection camera and an IR light detection camera. The cameras in the laparoscope 504 detect visible light images and fluorescent emission light images. Alternatively, the camera assembly 505 can contain other types of detectors that can accomplish the visible light image and fluorescent emission light image detection as cameras.

The visible light image and fluorescent image signals from the camera assembly 505 are processed by the camera controller 502. As with the fluorescent imaging module described above, the camera controller 504 can use any known technique to combine the fluorescent emission light image signals and visible image signals into a single display signal in order to overlay the two images in their proper alignment. In this case, since the two cameras are in an integral camera assembly 505, the cameras will have very little parallax error and can be factory aligned. The two image signals are then combined in a straightforward manner.

The cameras can also be aligned to a common focus point before surgery. Alternatively, software can be used to automatically detect common reference points within the two image signals in order to properly align the two images.

The camera controller 502 adjusts the display characteristics, such as color, of the fluorescent emission light image so it contrasts well with the visual light image so the surgeon can easily distinguish between the two images.

The display signal is sent to a video monitor 501 where the surgeon views the visible light image and the fluorescent image as a single overlaid image. The surgeon can instruct the camera controller 502 to display the fluorescent image in a desired color, shape, and texture so the fluorescent image is properly contrasted to the visible image.

Alternatively, the UV, visible, or IR fluorescence detector may be the same CCD device used for the detection of visible light. A single CCD can be used to detect both IR and visible light. The CCD may be controlled via a controller circuit to allow the detection of the emitted light signal either simultaneously or alternating with the visible light (interlaced detection). This detection may require the use of passive or active filters and a switching mechanism. Both the visible and the fluorescent emission light signals from the CCD would then be carried to an electronic circuit that would separate the fluorescent emission light signal and the visible light signal for separate digital processing.

Modern laparoscopic cameras usually have three CCD chips (red, blue, and green). A three-chip device can be used as described in the previous paragraph to detect both the visible and fluorescent emission light signals. Another alternative is to build a four-chip, five-chip, or greater number of chips, laparoscopic camera. Such a camera would contain three CCD chips for visible light detection plus any additional CCDs for detection of the fluorescent signal. The separate dedicated CCDs for the detection of the fluorescent emission light would be optimized for detecting light in the IR, NIR, visible or UV wavelengths. The detection could require active or passive filtering, and a switching controller. The advantage would be that the fluorescent emission light detector could be activated and filtered separately from the visible light controller.

In the case of a single, three-chip, four-chip, five-chip, or greater number of chip laparoscopic camera system, the entire assembly would attach to the laparoscope, endoscope, thoracoscope, or cystoscope either via a retractable housing on the viewing end, by being permanently designed as a component of the endoscope head, or by being miniaturized and placed on the tip of the endoscope in a "chip on the tip" configuration. In all of these cases, a separate collar, separator, or beam splitting box would not be needed. All optical manipulations would be carried out within the camera housing. The camera would be connected to its controller box via an electronic cable or wirelessly via Bluetooth (or any wireless technology) or a wireless local area network.

Figure 11:
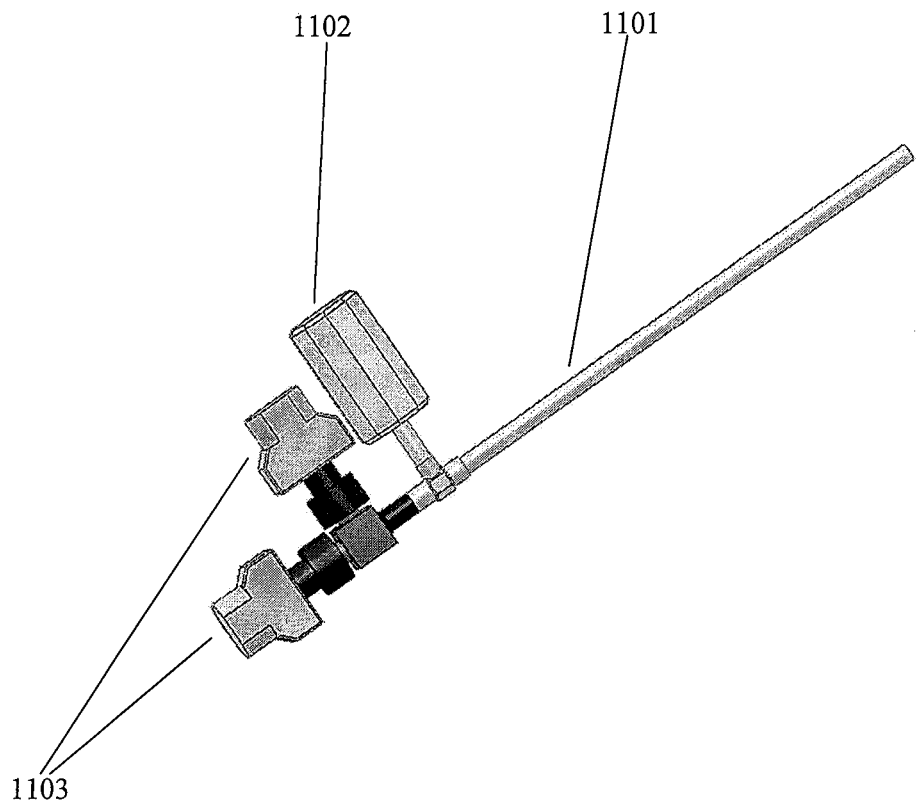
FIG. 11 is a diagram illustrating a laparoscope with an integral light source according to an embodiment of the invention.

FIG. 11 illustrates an embodiment of a laparoscope 1101 with an integral light source 1102 and cameras 1103 attached. The light source 1102 could be: a standard white light bulb, filtered light, lamp, LED, laser, etc. The light source 1102 may be powered by: an electric cord, an internal battery, or inductively coupled. Inside the body of the light source 1102 a lens system shapes the light beam to wide angle or narrow angle, which is selectable by the user.

A version of the light source may be cylindrical in nature and have a plurality of flat surfaces around it circumference. This shape has resistance to rolling because of the flat surfaces and helps prevent the light source 1102 from rolling off of a table when not attached to the laparoscope 1101.

3.2 Imaging System Optical Layout

Figure 6:
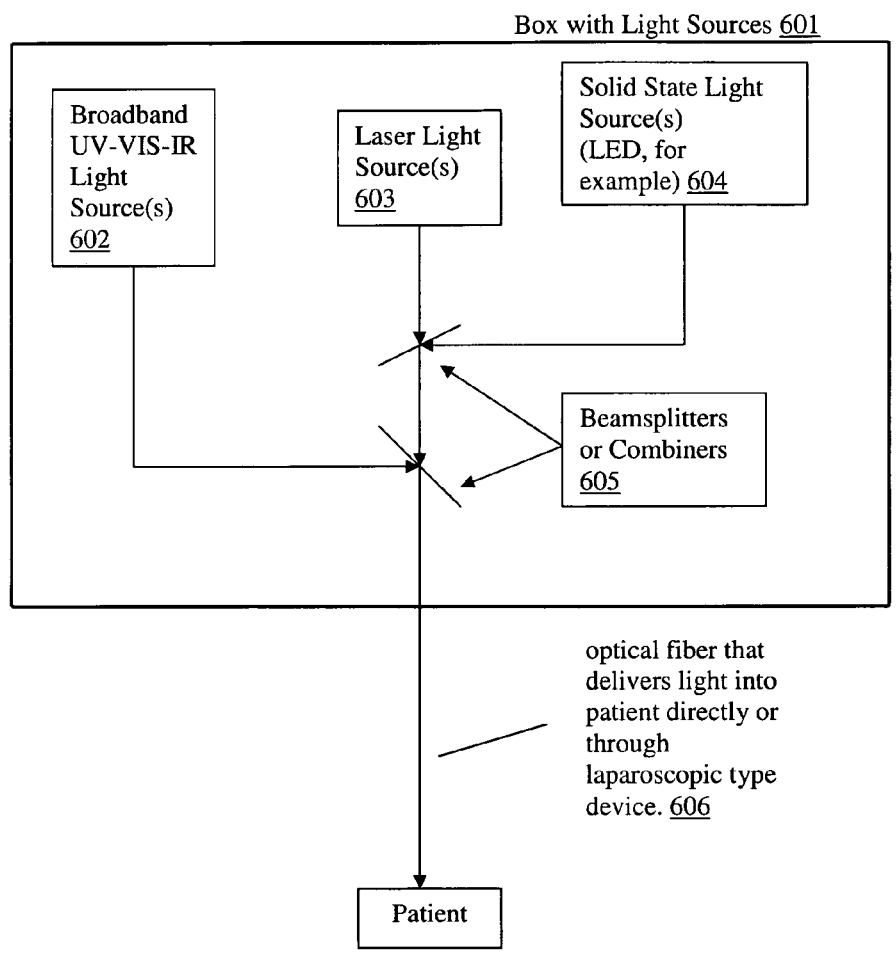
FIG. 6 is a diagram illustrating an optical layout for a laparoscopic lighting system according to an embodiment of the invention.

Referring to FIG. 6, in an embodiment, light from a broadband source 602 (this is used for the visual cameras) is combined with light that is used for navigation and targeting of the CBD 603, 604. The goal is to identify the CBD so as not to physically damage it during an operation on the gallbladder or removal of the gallbladder. The light used for identifying the CBD can be: monochromatic, comprised of multiple monochromatic sources, or be polychromatic. It may be randomly polarized, linearly polarized or circular polarized. The light source may be coherent or incoherent. Also, the light source may be constant wave or pulsed.

The light sources reside in an enclosure 601 (light box). Once the light sources are combined using a beamsplitter or combiner 605 they are directed into an optical fiber 606 (this could be a bundle of fibers). The optical fiber 606 is connected to the light box 606 on one end and to a connector on the laparoscope on the other end. The connector on the laparoscope has a fiber bundle attached to it. Once the light signals are in the fibers they are channeled through the laparoscope and exit into the patient. The light signals illuminate the abdominal cavity, in this case more specifically the: gallbladder, CBD, and nearby organs. This is the excitation path. Multiple lights sources can be used in the light box 601 that allow the excitation of multiple fluorescent dyes or auto-fluorescent tissue in the simultaneously or in rapid succession. If the wavelengths of two or more light sources overlap, then the overlapping light sources must be triggered alternately in order for the associated cameras to detect the proper fluorescent image. If there is no overlap, then the light sources may be simultaneously illuminated.

Organic materials have optical properties which are specific to that individual material. The system uses these unique properties to identify the CBD. In this case, the system detects fluorescence of the bile in the CBD, the bile in the CBD with a fluorescent dye added to the bile, or the auto-fluorescence of the tissue(s) itself.

Figure 7:
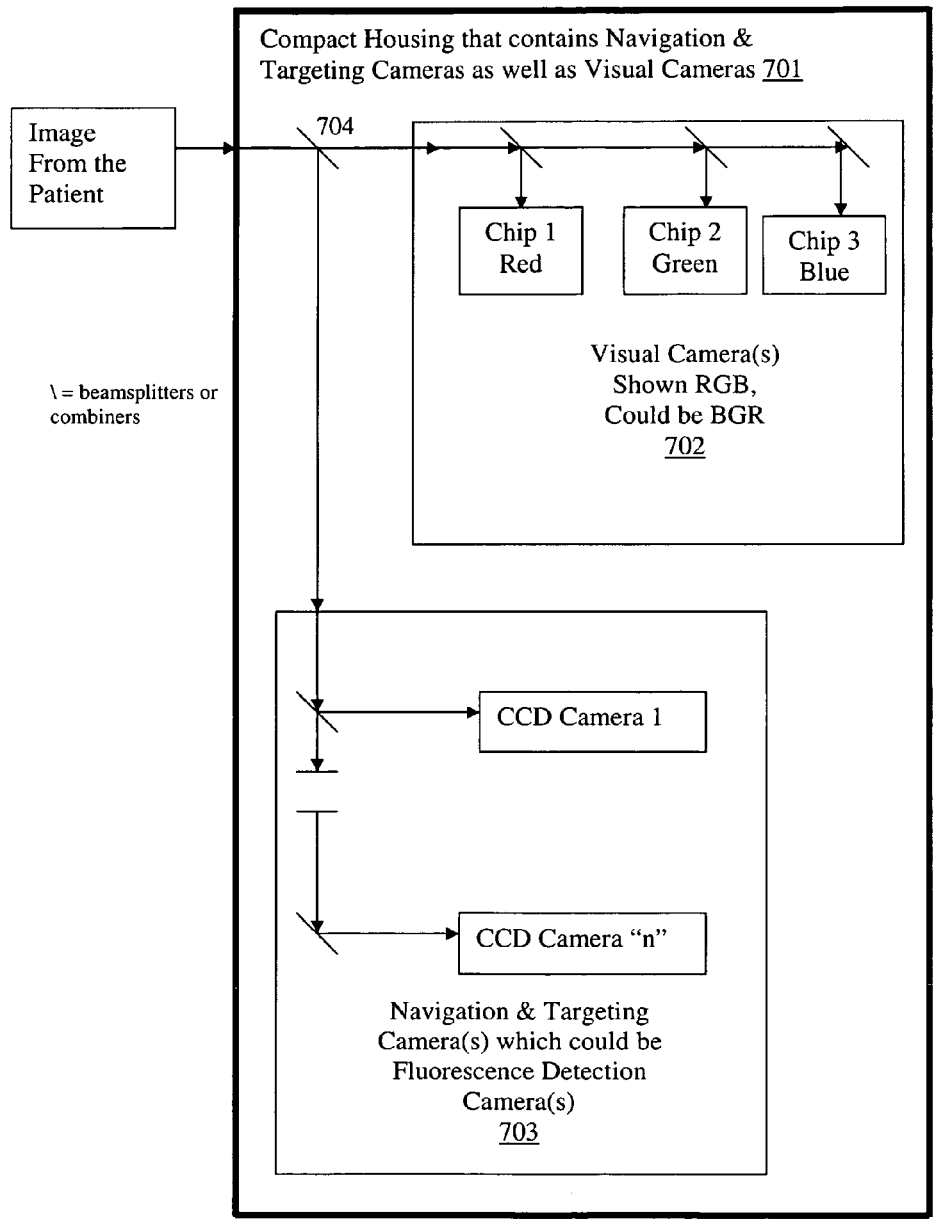
FIG. 7 is a diagram illustrating an optical layout for a laparoscopic camera system according to an embodiment of the invention.

The organic material absorbs a photon and then emits a photon at a longer wavelength (Stokes shifted). The emission is called fluorescent emission light and this can be collected by the laparoscope. There are a series of lenses that run the length of the tube in the shaft portion of the laparoscope. Referring to FIG. 7, the light is collected by the first lens and relayed to the other end of the device where it exits and can be accessed by a detector, in this case the light is split off with a beamsplitter 704 and directed to a camera(s) with special filter(s) which block all light except the fluorescent emission light 703. In this case these emissions are in the form of an image. The laparoscope also collects visual light as an image which can be seen by the human eye or preferably a camera. The visual light is split off by the beamsplitter 704 and directed to cameras that detect visual images 702. The cameras can be individual chips and the number of cameras can vary depending on the application. A focusing assembly (not shown) may be placed in front of the cameras 702, 703 in order to correct any beam distortion that occurs in the light path. The light is split off with beamsplitters to specific cameras.

The compact housing 701 is optional and may be used in the standalone embodiment described above in FIG. 5. If the add-on embodiment described in FIG. 4 is used, the compact housing 701 may not be implemented.

The two images, visual and fluorescent (i.e., navigation & targeting), are superimposed onto each other in real time so the surgeon can see the CBD and not damage it.

4.0 Common Bile Duct Fluorescence and Display

The CBD imaging system involves the following steps:
1. The placement of a fluorescent contrast material into the CBD.
2. Using a light source, that could be ultraviolet, infrared, or visible to excite the fluorescent material.
3. Detecting the fluorescence.
4. Processing the fluorescent image to remove artifact and scatter.
5. Displaying the live surgical image and the fluorescent image together in real-time with the CBD location clearly displayed for the surgeon on the monitor.

Placement of a Contrast Agent into the Bile Duct.

The fluorescent agent can be any agent that fluoresces in the ultraviolet, visible, or infrared (IR) range. The agent can be an optically active substance such as Indocyanine green (ICG), fluorescein, methylene blue, isosulfan blue, or any new fluorescent or color-based visualization media and markers. The fluorescent agent can be administered intravenously before or during the surgery if it is excreted into the bile (such as ICG). In the case of ICG, an administration kit comprised of a biomarker, a biocompatible solution for infusion, and the necessary tubing and instructions are provided. The time of preoperative IV administration of ICG is 40-60 minutes before the start of surgery. The ICG can be infused as part of a chemical "cocktail" that can optimize, enhance or change the ICG's optical properties.

Figure 8:
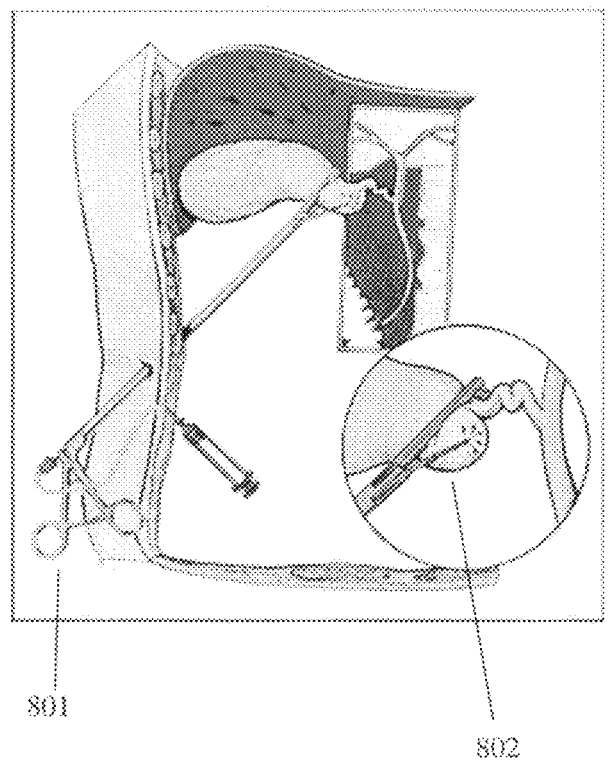
FIG. 8 is a block diagram illustrating a prior art implementation of a surgical instrument for injecting liquid into the gallbladder.

Referring to FIGS. 2 and 8, alternatively, the fluorescent contrast agent can be placed into the CBD via direct injection into the gallbladder 204, the cystic duct 205, or the CBD 201. Injecting the agent into the gallbladder has the advantages of ease, no need for prior dissection, and safety, as the gallbladder is away from the CBD. A specialized instrument 801 exists to inject liquid into the gallbladder 802 and then into the CBD (as described in U.S. Pat. No. 5,224,931).

As another alternative, a new laparoscopic instrument can be used specifically to inject fluorescent contrast material into the gallbladder. Such an instrument could have a 5 mm diameter shaft, jaws to hold the gallbladder, and a channel to inject the fluorescent material. This injection conduit may be separate from the jaws, or may traverse the jaws such that when the gallbladder is grasped, the fluorescent material can be injected directly into the gallbladder without spillage (much like a snake bite).

The fluorescent material could also be introduced into the CBD via the cystic duct 205 (the duct that connects the gallbladder to the CBD) instead of via the gallbladder 204. To do this, the cystic duct is dissected free in a standard manner for a standard intraoperative cholangiogram (IOC). An IOC catheter is placed into the cystic duct, secured, and the contrast agent is injected into the cystic duct and then into CBD. This last embodiment will result in imaging of the CBD, however it requires the previous successful dissection of the cystic duct, hence, exposing the patient to some, if not most, of the risk of the procedure prior to imaging the CBD.

Excitation of the Fluorescent Contrast Agent with a Light Energy Source.

Agents can be excited by light in different wavelengths including ultraviolet (UV), visual, or infrared (IR). The energy source can be one or more broad spectrum lamps, one or more lasers, or one or more light-emitting diodes (LEDs). The source will be referred herein as the narrow band energy source. Typically a narrow wavelength band in the UV, IR, or visible range is used to excite a specific fluorescent molecule. The narrow band energy source can be part of the laparoscopic light source or be enclosed in a separate housing with various methods used to direct the light to the tissues.

As described above, the narrow band energy source couples to the laparoscopic light source via an optical coupling box, thereby combining the visible and narrow band light in the existing fiberoptic cable that connects to the laparoscope. Alternatively, the narrow band light source can project the light onto the tissues via a completely separate lighting system such as a second laparoscope, a special light probe, or via one or more optically active trocars. The narrow band light source can produce light energy in one or more narrow wavelengths and its intensity and wavelength can be adjustable by the user.

If no fluorescent agent is being used, the narrow band energy source can be used to vary the type of visible light projected upon the surgical field. Light in one or multiple wavelengths, with or without white light, can be used to illuminate the surgical field. This effect can be used to enhance the contrast, depth, and differentiation of various tissues depending on their optical reflective, absorptive properties, and autofluorescence. If the light is projected from one or more separate sources (instead of, or in addition to, the laparoscope), the color, intensity, and spatial distribution of the light can be controlled and varied by the user to achieve various shadowing effects so as to enhance depth perception. A specialized electronic controller box is needed for this and the user can use a joystick, switch, or knobs to control the lighting factors mentioned. The use of combinations of various colors and intensities of light, along with varying the spatial distribution of the source of the light, can assist the surgeon with depth perception and tissue differentiation.

In an embodiment, the ICG infusion combined with the light generated from the IR laser/LED light source from the light box (described above), generates enough fluorescence to be imaged by existing laparoscopic camera systems without a having to add on an IR light detection camera to the laparoscope. Thus, the embodiment would add the ICG infusion/instrument delivery and the IR laser/LED light box as described above, but with no additional camera systems. The surgeon will be able to view the surgical field using the existing laparoscopic camera and monitor, and also view the fluorescent image of the CBD in the surgical field.

Detection of the Contrast Agent.

The fluorescent contrast agent is excited by the narrow band light energy and produces light emission in a certain wavelength band. This emitted energy can be captured by the endoscope, laparoscope, thoracoscope, cystoscope, surgical microscope, or a second optical probe introduced into the body cavity for this purpose. The light energy passing through the above-mentioned capture devices is then isolated, if needed, via a beam splitter or other light filtering device and directed to a detector. Methods for detecting the fluorescent contrast agent are discussed above. Certain filters may be used to filter non-desirable wavelengths of light from the collected light energy to enhance the detection of the fluorescent substance. The filters may be static or changeable, and may be controlled by an electronic controller.

Processing the Fluorescent Image.

Once detected and converted to a digital signal, the fluorescent emission light signal is passed through a microprocessor or computer to extract the critical tissue image information. This process may use software algorithms to enhance the image, to change the size, shape, and texture of the image, to change the color of the image, and/or to change the image to a computer generated graphic. All these parameters may adjustable by the user or set up into a predetermined set of choices to accommodate different user's preferences.

Displaying the Live Surgical Image and the Fluorescent Image.

Figure 9:
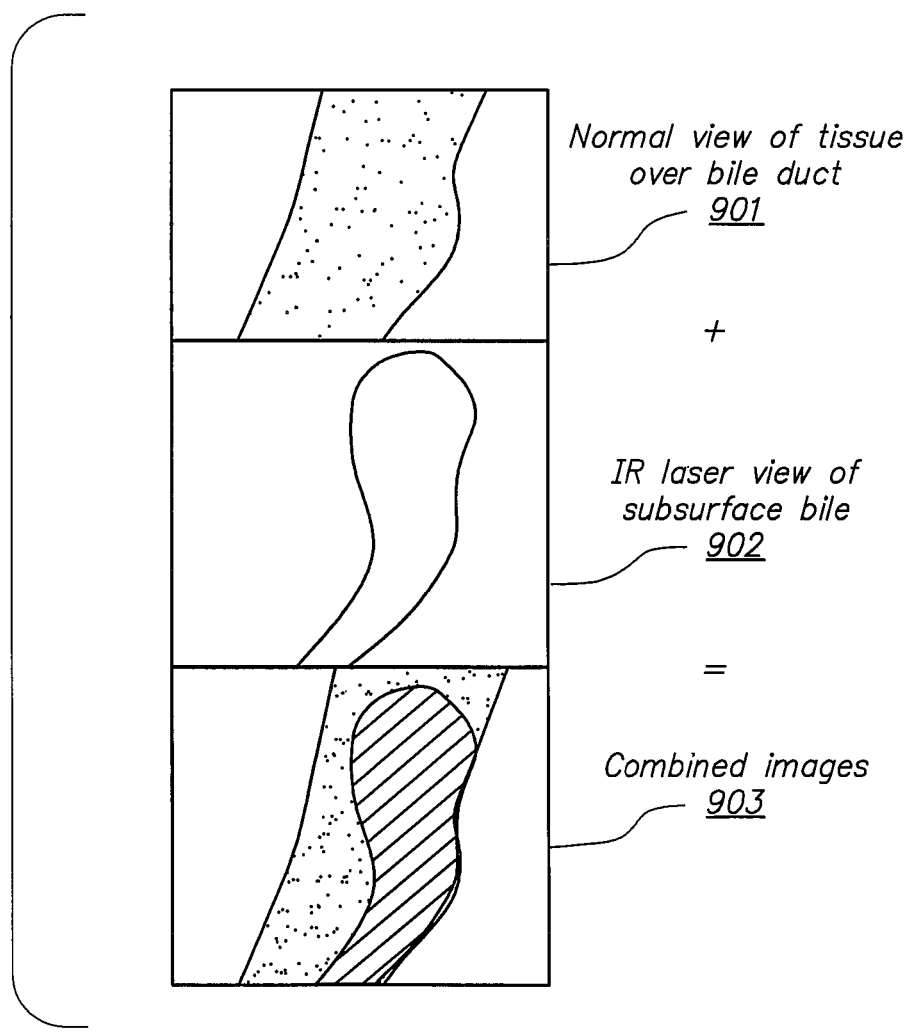
FIG. 9 is a block diagram illustrating overlaying of visual light images with fluorescent emission light images into a single display according to an embodiment of the invention.

Referring to FIG. 9, a series of images showing visible light images and fluorescent emission light images is shown. The digital output from the processed fluorescent emission light signal is digitally combined with the visual light image in order to create a seamless overlay of both images. The combining and/or overlaying of the images can be performed by software in a computer or microprocessor. The parameters of the overlay and the presence of each image layer is user selectable.

The combined visual/fluorescent image is displayed on an existing standard laparoscopic CRT, display, video monitor, flat panel display, projector, or head-mounted display. The combined digital image is output in a format compatible with standard monitors on the market today. The overlay image can be turned on or off by the user via a switch or software control which could alternatively be voice activated. The overlay image presents the images in a manner that the surgeon can see the location of the CBD via the fluorescent emission from any normal visual angle while he is working. Some surgeons may prefer to have two monitors, one without the overlay image and one with the overlay image. The system can handle multiple displays with different combinations of images. The system can also display an overlay image with the visual light image shown in a picture in a picture mode where either image can be shown as the main image and the other as the smaller image in the sub-picture display.

A visible light image 901 of tissue over a bile duct and an artery is shown without an overlay. The fluorescent image 902 of the bile duct and artery is shown, also without an overlay. The two types of images do not convey enough information to the surgeon alone. The combination of the two images allows the surgeon to picture what is under the tissue as well as the tissue itself. The normal and enhanced bile duct images are displayed together in a natural overlaid manner 903 on the surgical image so the CBD is visible to the surgeon despite being under the overlying tissue. The surgeon can now avoid injuring the CBD using the overlaid images.

When the image overlay is activated, the visible light image may be altered in color and/or intensity to highlight the fluorescent image. The fluorescent image can be changed to any desirable color by the user. The fluorescent image is easily enhanced due to the fluorescent image being only what is fluorescent in the body cavity.

The software for image processing allows the user to configure and control the CBD visualization system before, during, and after surgery. The control may be carried out via a computer keyboard, a specialized key pad, touch screen, foot-pedal, voice control, a head-up display, etc. The control may be provided to the surgeon in a sterile enclosure such as a plastic cover, on the floor as a foot pedal, or may be used by the circulating nurse in a non-sterile setting.

The computer used for the digital processing of images and control of the image detection can include software and hardware for recording the combined visual and fluorescent images on an external or internal digital recording device such as CD, DVD, optical disk, hard disk, or flash memory. The capacity to print static combined images onto photo paper can be included in the system. The system can provide an Ethernet connection to allow Internet or intranet connectivity so that recordings may be made to a server or transmitted over the Internet or intranet for training purposes.

NOTES Application.

Natural Orifice Translumenal Endoscopic Surgery (NOTES)™ was developed several years ago in response to the concepts that patients would: 1) realize the benefits of less invasive surgery by reducing the recovery time; 2) experience less physical discomfort associated with traditional procedures; and 3) have virtually no visible scarring following this type of surgery. All of these advantages have spurred research and investigation forward, encouraging physicians and researchers to develop new equipment and techniques to use during NOTES procedures.

As an example, in natural orifice surgery the gallbladder might be removed through the mouth. The doctor would insert a tube down the esophagus, make a small incision in the stomach or digestive tract to gain access to the abdominal cavity and take the organ out by the same route. Some operations might be done via the rectum, vagina, urethra or bladder as well.

One of the main problems with NOTES surgery is spatial orientation and visualization. This is due to the changing visual axis that the flexible endoscope adopts while inserted into the peritoneal cavity. Additionally, the quality of the endoscopic visual image is usually inferior to standard laparoscopic systems.

During NOTES gallbladder surgery, the surgeon may use a top-down approach to removing the gallbladder, thus dissecting the gallbladder down to a single pedicle of tissue where the critical ductal structure is located. At this point, if the surgeon could clearly see the location of the common bile duct, he could safely ligate or clip the pedicle and conclude the surgery in less time and with less effort. Alternatively, visualization of the common bile duct would be helpful during NOTES gallbladder surgery during the dissection of the cystic duct and arteries because of the limitations in visualization and manipulation with current NOTES systems. In both cases, clear visualization of the common bile duct would make NOTES gallbladder surgery faster and safer for the patient.

In an embodiment, the bile duct vision system operates in an identical manner to the laparoscopic application described above. The fluorescent excitation light is introduced into the fiberoptic system of the flexible endoscope. A beam-splitter collar and separate fluorescent excitation camera system attached to the endoscope would be used to capture the fluorescent image. The fluorescent image would be processed and both images displayed in: overlay mode, picture in a picture, or side by side formats (all described above), to the surgical team. In a fully integrated NOTES platform, the fluorescent excitation source and camera are integrated into the endoscopic equipment system. In a NOTES application, the ICG or other fluorescent or color marker would be introduced into the common bile duct either via IV injection prior to surgery or by direct injection into the gallbladder during surgery. The direct injection could be done with existing endoscopic injection needle catheters, a percutaneous needle, or a newly designed instrument or catheter for the injection.

In an embodiment, the displayed images are expanded past the two-dimensional arena. The embodiment displays a three-dimensional image to the surgeon. The surgeon or assistant has the ability to rotate the images using a remote control or using a command device on the laparoscope, endoscope, thoracoscope, cystoscope, etc.

5.0 Hardware Overview

Figure 10:
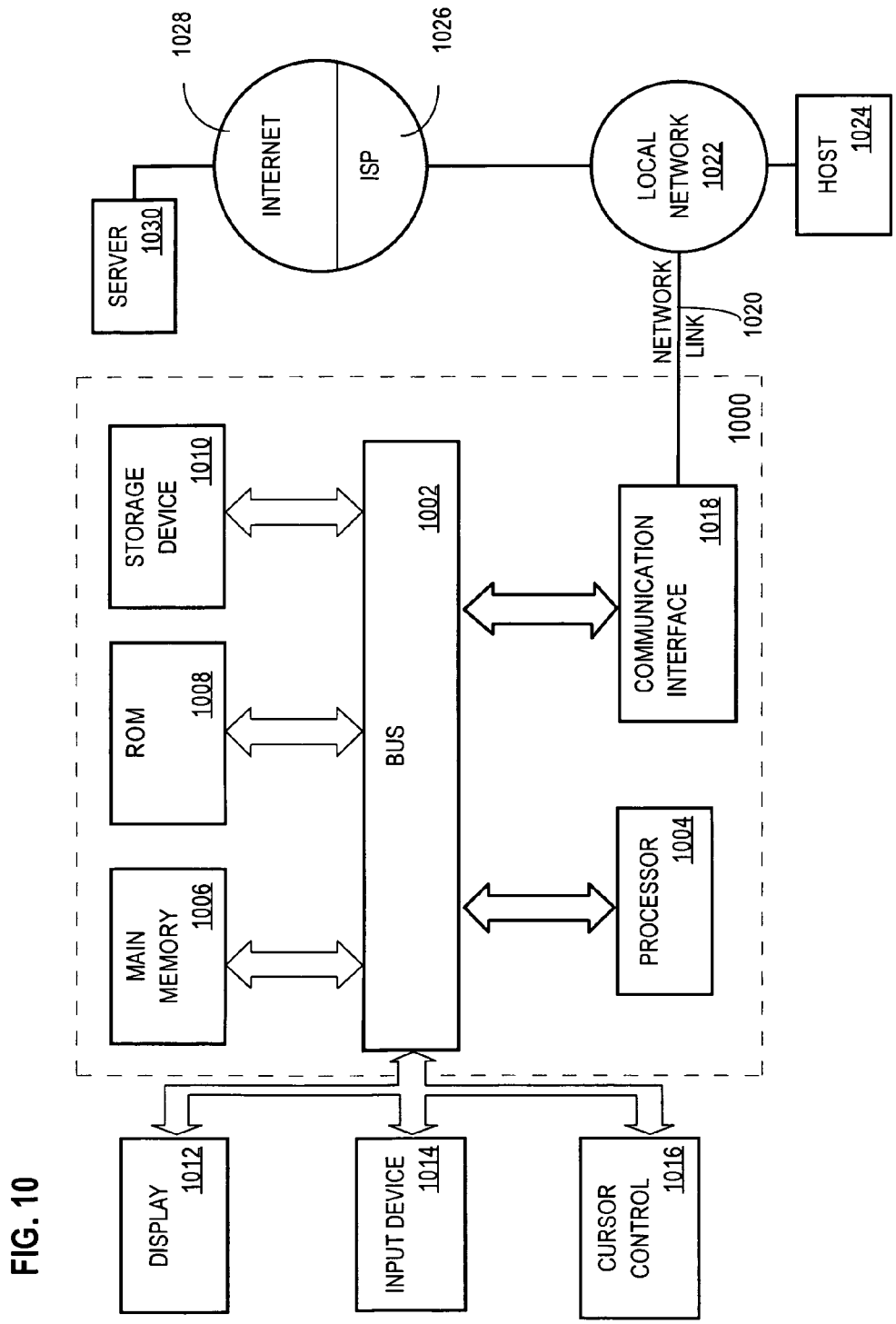
FIG. 10 is a block diagram that illustrates a computer system upon which an embodiment may be implemented.

FIG. 10 is a block diagram that illustrates a computer system 1000 upon which an embodiment of the invention may be implemented. Computer system 1000 includes a bus 1002 or other communication mechanism for communicating information, and a processor 1004 coupled with bus 1002 for processing information. Computer system 1000 also includes a main memory 1006, such as a random access memory (RAM) or other dynamic storage device, coupled to bus 1002 for storing information and instructions to be executed by processor 1004. Main memory 1006 also may be used for storing temporary variables or other intermediate information during execution of instructions to be executed by processor 1004. Computer system 1000 further includes a read only memory (ROM) 1008 or other static storage device coupled to bus 1002 for storing static information and instructions for processor 1004. A storage device 1010, such as a magnetic disk or optical disk, is provided and coupled to bus 1002 for storing information and instructions.

Computer system 1000 may be coupled via bus 1002 to a display 1012, such as a cathode ray tube (CRT), projection, head-mounted display or flat panel display for displaying information to a computer user. An input device 1014, including alphanumeric and other keys, is coupled to bus 1002 for communicating information and command selections to processor 1004. Another type of user input device is cursor control 1016, such as a mouse, a trackball, or cursor direction keys for communicating direction information and command selections to processor 1004 and for controlling cursor movement on display 1012. This input device typically has two degrees of freedom in two axes, a first axis (e.g., x) and a second axis (e.g., y), that allows the device to specify positions in a plane.

The invention is related to the use of computer system 1000 for implementing the techniques described herein. According to one embodiment of the invention, those techniques are performed by computer system 1000 in response to processor 1004 executing one or more sequences of one or more instructions contained in main memory 1006. Such instructions may be read into main memory 1006 from another machine-readable medium, such as storage device 1010. Execution of the sequences of instructions contained in main memory 1006 causes processor 1004 to perform the process steps described herein. In alternative embodiments, hard-wired circuitry may be used in place of or in combination with software instructions to implement the invention. Thus, embodiments of the invention are not limited to any specific combination of hardware circuitry and software.

The term "machine-readable medium" as used herein refers to any medium that participates in providing data that causes a machine to operation in a specific fashion. In an embodiment implemented using computer system 1000, various machine-readable media are involved, for example, in providing instructions to processor 1004 for execution. Such a medium may take many forms, including but not limited to storage media and transmission media. Storage media includes both non-volatile media and volatile media. Non-volatile media includes, for example, optical or magnetic disks, such as storage device 1010. Volatile media includes dynamic memory, such as main memory 1006. Transmission media includes coaxial cables, copper wire and fiber optics, including the wires that comprise bus 1002.

Common forms of machine-readable media include, for example, a floppy disk, a flexible disk, hard disk, magnetic tape, or any other magnetic medium, a CD/DVD, any other optical medium, punchcards, papertape, any other physical medium with patterns of holes, a RAM, a PROM, and EPROM, a FLASH-EPROM, any other memory chip or cartridge, or any other medium from which a computer can read.

Various forms of machine-readable media may be involved in carrying one or more sequences of one or more instructions to processor 1004 for execution. For example, the instructions may initially be carried on a magnetic disk of a remote computer. The remote computer can load the instructions into its dynamic memory and send the instructions over a telephone line using a modem. A modem local to computer system 1000 can receive the data on the telephone line and use an infra-red transmitter to convert the data to an infra-red signal. An infra-red detector can receive the data carried in the infra-red signal and appropriate circuitry can place the data on bus 1002. Bus 1002 carries the data to main memory 1006, from which processor 1004 retrieves and executes the instructions. The instructions received by main memory 1006 may optionally be stored on storage device 1010 either before or after execution by processor 1004.

Computer system 1000 also includes a communication interface 1018 coupled to bus 1002. Communication interface 1018 provides a two-way data communication coupling to a network link 1020 that is connected to a local network 1022. For example, communication interface 1018 may be an integrated services digital network (ISDN) card or a modem to provide a data communication connection to a corresponding type of telephone line. As another example, communication interface 1018 may be a local area network (LAN) card to provide a data communication connection to a compatible LAN. Wireless links may also be implemented. In any such implementation, communication interface 1018 sends and receives electrical, electromagnetic or optical signals that carry digital data streams representing various types of information.

Network link 1020 typically provides data communication through one or more networks to other data devices. For example, network link 1020 may provide a connection through local network 1022 to a host computer 1024 or to data equipment operated by an Internet Service Provider (ISP) 1026. ISP 1026 in turn provides data communication services through the world wide packet data communication network now commonly referred to as the "Internet" 1028. Local network 1022 and Internet 1028 both use electrical, electromagnetic or optical signals that carry digital data streams.

Computer system 1000 can send messages and receive data, including program code, through the network(s), network link 1020 and communication interface 1018. In the Internet example, a server 1030 might transmit a requested code for an application program through Internet 1028, ISP 1026, local network 1022 and communication interface 1018.

The received code may be executed by processor 1004 as it is received, and/or stored in storage device 1010, or other non-volatile storage for later execution. In this manner, computer system 1000 may obtain application code in the form of a carrier wave.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A method for imaging with a laparoscope, said method comprising:
   providing a laparoscope having a visible light camera at a proximal end thereof and a light channel with optics for transmitting illumination to a surgical field and receiving images from the surgical field;
   attaching a fluorescence detection coupler to the proximal end of the laparoscope in series between the visible light camera and the proximal end of the laparoscope;
   introducing a distal end of the laparoscope to the surgical field;
   delivering visible light and fluorescent excitation light simultaneously through the light channel to illuminate the surgical field;
   returning a visible light image and a fluorescent light image from the surgical field through the optics to the fluorescence detection coupler, wherein the fluorescence detection coupler produces fluorescence image data and wherein the visible light images passes through the fluorescence detection coupler to the visible light camera which produces visible light image data; and
   displaying the fluorescence image overlaid over the visible light image on a display screen in real time based on the visible light image data and the fluorescence image data.

2. A method as in claim 1, further comprising delivering a fluorescent agent to an organ to be imaged.

3. a method as in claim 2, wherein the fluorescent agent fluoresces in the ultraviolet, visible or infrared range.

4. A method as in claim 2, wherein the organ is the common bile duct.

5. A method as in claim 4, wherein the distal end of the laparoscope is introduced to the abdomen.

6. A method as in claim 1, wherein displaying comprises aligning common reference points on the images to align the fluorescent and visible light images.

7. A method as in claim 1, wherein the fluorescence detection coupler and the visible light camera are attached in-line.

8. A method as in claim 1, wherein delivering visible light and fluorescent light comprises providing a single module that includes both a fluorescent light source and a visible light source and delivering light from both sources through a common optical connection to the laparoscope.

9. A method as in claim 1, wherein delivering visible light and fluorescent light comprises providing separate modules and delivering fluorescent light from one module to the laparoscope and delivering visible light from another module to the laparoscope.

* * * * *